(12) United States Patent
Hideno et al.

(10) Patent No.: US 8,591,728 B2
(45) Date of Patent: Nov. 26, 2013

(54) FILTER UNIT, FLUID REFILL APPARATUS, AND ELECTRONIC DEVICE TEST APPARATUS

(75) Inventors: Seiji Hideno, Tokyo (JP); Seigo Matsunaga, Tokyo (JP)

(73) Assignee: Advantest Corporation, Tokyo (JP)

( * ) Notice: Subject to any disclaimer, the term of this patent is extended or adjusted under 35 U.S.C. 154(b) by 1208 days.

(21) Appl. No.: 12/066,562

(22) PCT Filed: Aug. 23, 2006

(86) PCT No.: PCT/JP2006/316498
§ 371 (c)(1),
(2), (4) Date: Mar. 12, 2008

(87) PCT Pub. No.: WO2007/032186
PCT Pub. Date: Mar. 22, 2007

(65) Prior Publication Data
US 2009/0126468 A1 May 21, 2009

(30) Foreign Application Priority Data

Sep. 16, 2005 (JP) .................................. 2005-270858
Apr. 13, 2006 (JP) .................................. 2006-111388

(51) Int. Cl.
*B01D 35/02* (2006.01)
*G01N 27/10* (2006.01)
*G08B 21/00* (2006.01)

(52) U.S. Cl.
USPC ............ 210/85; 210/96.1; 210/143; 210/243; 210/257.1; 210/258; 374/45; 374/57; 438/14

(58) Field of Classification Search
USPC .................. 210/85, 86, 94, 96.1, 295, 266, 210/314–317, 323.1, 323.2, 167.02, 222, 210/223, 243, 499, 503, 505, 143, 257.1, 210/258, 497.01; 184/6.21, 6.24; 96/417; 73/53.05, 53.06, 61.43; 204/400; 324/439, 446, 449; 374/45, 57; 438/14, 438/54

See application file for complete search history.

(56) References Cited

U.S. PATENT DOCUMENTS 2,048,350 A * 7/1936 McLean ........................ 210/238
3,878,103 A * 4/1975 Miller et al. .................. 210/243

(Continued)

FOREIGN PATENT DOCUMENTS

JP        61-90046      5/1986
JP        61-128504     6/1986

(Continued)

OTHER PUBLICATIONS

English language Abstract of JP 63-262547.

(Continued)

*Primary Examiner* — Joseph Drodge
(74) *Attorney, Agent, or Firm* — Greenblum & Bernstein P.L.C.

(57) ABSTRACT

A conductive fluid detection apparatus for detecting moisture mixed into a coolant comprises: a filter unit having a tubular member through which a coolant can flow, mesh members made of stainless steel etc. and filter paper through which the coolant can pass, but which can hold moisture, the mesh members and the filter paper provided and stacked inside the tubular member, the filter paper interposed between the mesh members; a resistance value measurement circuit measuring the resistance value between mesh members; and a relay stopping the supply of power to the pump when the resistance value between the mesh members falls.

7 Claims, 6 Drawing Sheets

(56) References Cited

U.S. PATENT DOCUMENTS

| | | | |
|---|---|---|---|
| 3,909,383 A * | 9/1975 | Sato | 210/665 |
| 4,129,501 A * | 12/1978 | Haynes | 210/689 |
| 4,594,138 A * | 6/1986 | Thompson | 204/665 |
| 4,955,726 A * | 9/1990 | Bargigia et al. | 374/57 |
| 5,167,451 A * | 12/1992 | Muller et al. | 374/45 |
| 5,242,587 A * | 9/1993 | Barrington et al. | 210/223 |
| 5,290,101 A * | 3/1994 | Englert et al. | 374/57 |
| 5,294,199 A * | 3/1994 | Boersen et al. | 374/57 |
| 5,342,514 A * | 8/1994 | Turner et al. | 204/627 |
| 5,523,692 A * | 6/1996 | Kuroyanagi et al. | 324/438 |
| 5,613,776 A * | 3/1997 | Turner et al. | 374/57 |
| 6,406,622 B1 * | 6/2002 | Tsuihiji et al. | 210/193 |
| 6,718,819 B2 * | 4/2004 | Schoess | 73/53.05 |
| 7,726,145 B2 * | 6/2010 | Nakamura | 62/259.2 |
| 2005/0194309 A1 * | 9/2005 | Harenbrock et al. | 210/500.1 |
| 2006/0276156 A1 | 12/2006 | Nakada et al. | |

FOREIGN PATENT DOCUMENTS

| | | |
|---|---|---|
| JP | 5-50355 | 7/1996 |
| JP | 2567604 | 10/1996 |
| JP | 9-152411 | 6/1997 |

OTHER PUBLICATIONS

English language Abstract of JP 61-128504.
English language Abstract of JP 9-152411.
English language Abstract of JP 61-90046.
Japanese Official Action dated Sep. 13, 2011.

* cited by examiner

FILTER UNIT, FLUID REFILL APPARATUS, AND ELECTRONIC DEVICE TEST APPARATUS

TECHNICAL FIELD

The present invention relates to a filter unit used for a conductive fluid detection apparatus for detecting a conductive fluid (for example moisture etc.) mixed into an insulating fluid (for example a fluorine-based inert liquid etc.) and a conductive fluid detection apparatus using that filter unit.

BACKGROUND ART

FIG. 6 is a schematic perspective view showing a conventional method of refilling a chiller with a coolant.

In the process of production of semiconductor devices, an electronic device test system 1 is required for testing the IC chips and other electronic devices which are finally produced. These types of electronic devices are tested by setting the test environment to a temperature environment of an ordinary temperature, a high temperature, or a low temperature, inputting test patterns to the IC chips for operation, and inspecting the response patterns. This is because, as the IC chip properties, it is necessary to guarantee that the chips operate well at an ordinary temperature or high temperature or low temperature.

A general electronic device test system 1 comprises: a tester 2 storing a program for sending out a test pattern and inspecting a response pattern; a test head 5 having contact terminals for electrically connecting this tester and devices under test (DUT); and a handler (not shown) successively conveying a large number of devices under test to contact terminals of the test head and physically classifying devices under test finished being tested in accordance with the test results. Further, the devices under test are set in a handler and conveyed to the test head 5, then the devices under test are pushed against the contact terminals of the test head 5 to electrically connect them and perform the target operational tests.

The test head 5 of this electronic device test system, as shown in FIG. 6, has a large number of pin electronic cards 6 used as interfaces for the input/output terminals of the electronic devices. A large number of LSI or other various types of devices for measurement are mounted on the pin electronics cards 6. Note that, for convenience in explanation, FIG. 6 shows the state of pulling up one of the pin electronics cards 6 provided at the test head 5.

The various types of devices mounted at the pin electronics card 6 become a high temperature due to the self-generated heat at the time of testing the electronic devices, so, as shown in the figures, the surface of the pin electronics card 6 is covered by a water jacket 7. Further, the fluorine-based inert liquid or other coolant cooled by a chiller 3 is circulated inside the water jacket 7 and brought into direct contact with the heat emitting devices to cool the self-heat emitting devices.

By the way, this coolant is refilled in the chiller 3 by using a manual or electric pump 8 to inject the coolant from a container 9 to a tank 4 of the chiller 3. At the time of this refilling, sometimes the containers 4 are mistaken and not a coolant, but distilled water ends up being poured into the tank 4 or moisture ends up being mixed in the coolant. If moisture enters the water jacket 7 covering the pin electronics card 6, the heating emitting devices on the card 6 will be electrolytically corroded and will no longer be able to be repaired, thereby necessitating replacement of the card 6 itself. In particular, the water jackets 7 of cards 6 provided at the test head 5 are connected by a single cooling path, so once moisture enters this cooling path, all the cards 6 will have to be replaced and serious damages will be incurred.

DISCLOSURE OF THE INVENTION

The present invention has as its object the provision of a filter unit used for a conductive fluid detection apparatus able to detect a conductive fluid mixed into an insulating fluid and of a conductive fluid detection apparatus using the same.

To achieve this object, according to the present invention, there is provided a filter unit used for a conductive fluid detection apparatus for detecting a conductive fluid mixed into an insulating fluid, comprising: two or more conductive members made of a conductive material and through which the insulating fluid and the conductive fluid can pass.

In the present invention, when a conductive fluid mixed into an insulating fluid passes between two or more conductive members, the conductive fluid conductively connects the conductive members, so it is possible to detect the intermixture of conductive fluid based on this conductive connection.

While not particularly limited in the present invention, preferably the filter unit further comprises a tubular member through which the insulating fluid flows from an upstream side to a downstream side and a holding member through which the insulating fluid can pass and able to hold the conductive fluid, and the two or more conductive members and the holding member are provided and stacked inside the tubular member, and the holding member is interposed between the conductive members.

In the present invention, inside the tubular member through which the insulating fluid can pass, two or more conductive members through which the insulating fluid and the conductive fluid can pass and a holding member through which the insulating fluid can pass and able to hold the conductive fluid are provided. These members are stacked in the state with a holding member interposed between two or more conductive members. When the conductive fluid mixed into an insulating fluid is held in the holding member, the held conductive fluid conductively connects the conductive members, so it is possible to detect the mixture of a conductive fluid based on this conductive connection.

While not particularly limited in the present invention, preferably the conductive members are mesh members made of stainless steel. By forming the conductive members by stainless steel, rusting is difficult, so it is possible to maintain a good detection precision.

While not particularly limited in the present invention, the holding member is preferably filter paper.

While not particularly limited in the present invention, the filter unit preferably further comprises an adsorption member able to adsorb the conductive fluid, and the adsorption member is provided inside the tubular member at the downstream side from the holding member.

By providing an adsorption member able to adsorb a conductive fluid at the downstream side from the holding member, even if conductive fluid flows to the downstream side from the holding member, it is possible to prevent the conductive fluid from flowing into the tank of the chiller. Further, this adsorption member can maintain the drying of the holding member.

As the adsorption member, for example zeolite or silica gel can be cited.

While not particularly limited in the present invention, preferably the two or more conductive members are provided inside of the tank in which the insulating fluid is stored so that the insulating fluid heading toward the outlet of the tank passes through the two or more conductive members. Due to this, it becomes possible to detect conductive fluid mixed in the tank storing the insulating fluid.

While not particularly limited in the present invention, preferably the two or more conductive members are provided so as to surround the outlet.

While not particularly limited in the present invention, the two or more conductive members form a tubular member surrounding the outlet. The topmost end of the tubular member is preferably set higher than the upper limit of the liquid surface of the insulating fluid stored in the tank.

While not particularly limited in the present invention, preferably the two or more conductive members include first conductive members and second conductive members extending along a height direction, and the first conductive members and the second conductive members are alternately arranged along the circumferential direction.

As the insulating fluid, for example a fluorine-based inert liquid can be cited. As the conductive fluid, for example water can be cited.

To achieve the above object, according to the present invention, there is provided a conductive fluid detection apparatus for detecting a conductive fluid mixed into an insulating fluid, comprising: any of the above filter units and a judging means for judging that the conductive fluid is mixed into the insulating fluid when the conductive members are conductively connected.

In the present invention, when the conductive fluid mixed into an insulating fluid is held by the holding member, the held conductive fluid conductively connects the conductive members, so the judging means judges that the insulating fluid has a conductive fluid mixed in based on this conductive connection.

While not particularly limited in the present invention, the judging means preferably judges that the conductive fluid is mixed into the insulating fluid based on the resistance value between the conductive members.

While not particularly limited in the present invention, preferably the apparatus further comprises supplying means for supplying the insulating fluid to the filter unit, and the judging means stops the supply of the insulating fluid by the supplying means when detecting the mixture of the conductive fluid into the insulating fluid.

When the conductive fluid is mixed into an insulating fluid, the judging means can make the supplying means stop so as to prevent the conductive fluid mixed into the insulating fluid from flowing into the tank of the chiller. Further, even when conductive film is mixed into the tank holding the insulating fluid, it is possible to prevent the outflow of conductive fluid from the tank to inside the circulation system.

While not particularly limited in the present invention, preferably the apparatus further comprises an alarm means for issuing an alarm when the judging means detects the mixture of the conductive fluid into the insulating fluid.

DESCRIPTION OF NOTATIONS

Figure 1:
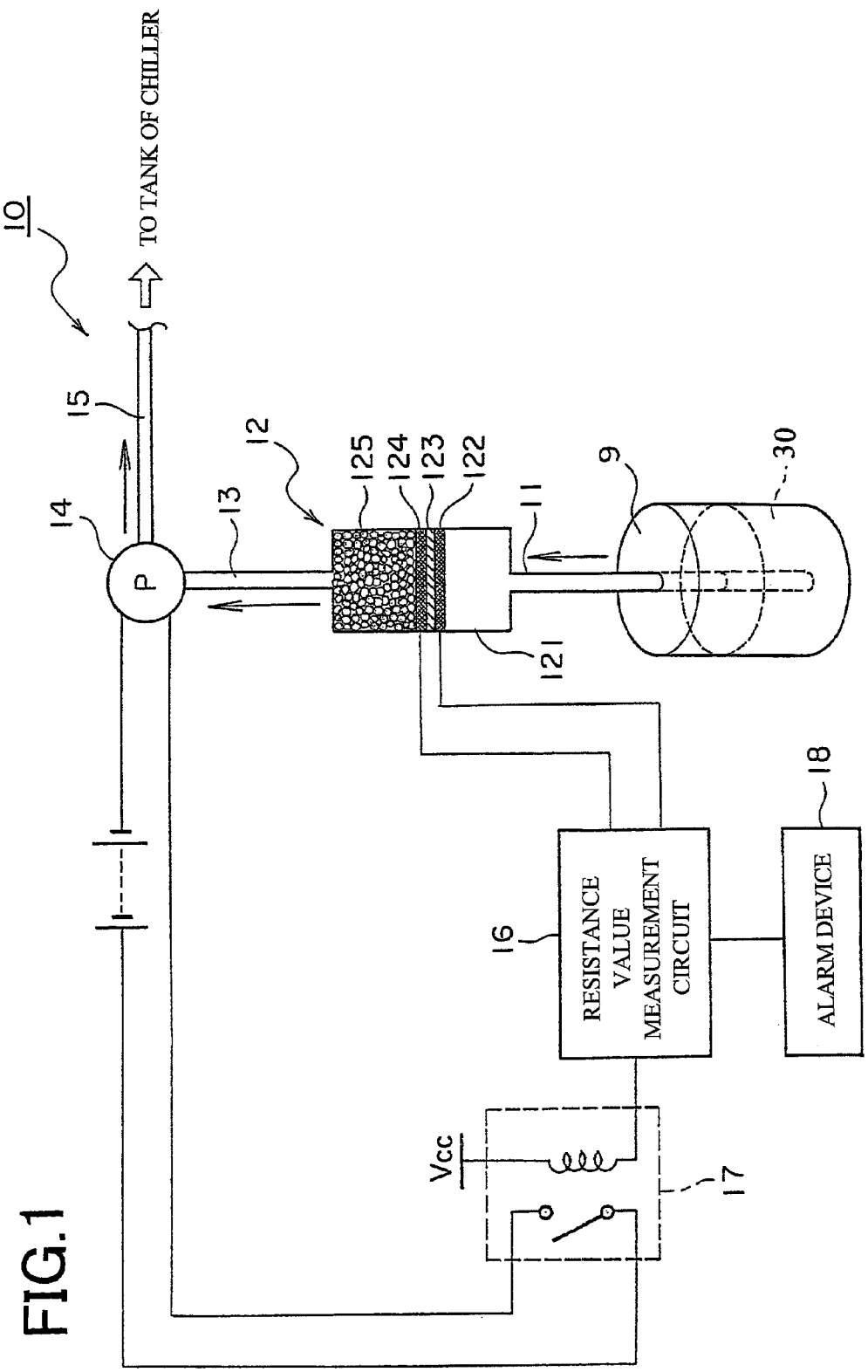
FIG. 1 is a conceptual view showing the overall configuration of a conductive fluid detection apparatus according to a first embodiment of the present invention.

1 . . . electronic device test system
2 . . . tester
3 . . . chiller
3a . . . pump
3b . . . supply side pipe
3c return side pipe
4 . . . tank
4a . . . inlet
4b . . . outlet
5 . . . test head
6 . . . pin electronics card
7 . . . water jacket
8 . . . pump
9 . . . container
10 . . . conductive fluid detection apparatus
11 . . . first pipe
12 . . . filter unit
121 . . . tubular member
122 . . . upstream side mesh member
123 . . . filter paper
123a . . . part of filter paper trapping moisture
124 . . . downstream side mesh member
125 . . . zeolite
13 . . . second pipe
14 . . . pump
15 . . . third pipe
16 . . . resistance value detection circuit
17 . . . relay
18 . . . alarm device
20 . . . conductive fluid detection apparatus
21 . . . filter unit
22 . . . tubular member
23 . . . first conductive wire
23a . . . first connecting member
24 . . . second conductive wire
24a . . . second connecting member
25 . . . insulating wire
26 . . . mount
26a . . . through hole
27 . . . resistance value detection circuit
28 . . . relay
29 . . . alarm means
30 . . . coolant
R . . . falling resistance value
W . . . passing moisture

BEST MODE FOR CARRYING OUT THE INVENTION

Below, embodiments of the present invention will be explained based on the drawings.

First Embodiment

Figure 2:
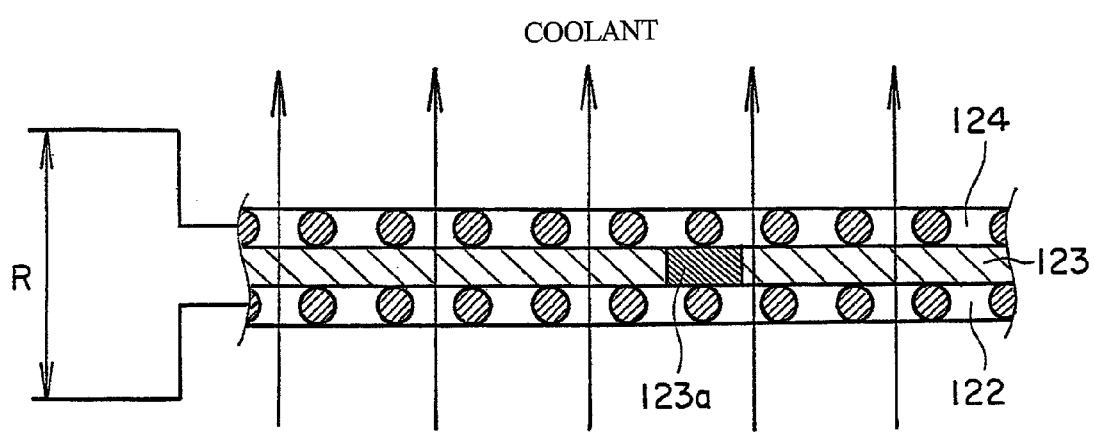
FIG. 2 is a cross-sectional view of principal parts for explaining a method of detection by a conductive fluid detection apparatus shown in FIG. 1.

FIG. 1 is a conceptual view showing the overall configuration of a conductive fluid detection apparatus according to a first embodiment of the present invention, while FIG. 2 is a cross-sectional view of principal parts for explaining a method of detection by the conductive fluid detection apparatus shown in FIG. 1.

The conductive fluid detection apparatus 10 according to the first embodiment of the present invention, as shown in FIG. 1, is a apparatus for detecting moisture mixed in a coolant 30 when refilling the coolant 30 stored in a container 9 into a tank 4 of a chiller 3. This apparatus comprises: a coolant injection system having a first pipe 11, filter unit 12, second pipe 13, pump 14 and third pipe 15; and a control system having a resistance value measurement circuit 16, relay 17 and alarm device 18.

This detection apparatus 10, by driving the pump 15, supplies the coolant 30 through the first pipe 11 from the container 9 to the inside of the filter unit 12, inspects for mixture of moisture in the filter unit 12, then supplies the coolant through the second and third pipes 13 and 15 to the tank 4 of the chiller 3. As the coolant 3 injected from the detection apparatus 10 according to the present embodiment into the tank 4 of the chiller 3, for example 3M's Fluorinert (registered trademark) or another fluorine-based inert liquid may be mentioned.

The filter unit 12 in the present embodiment comprises a tubular member 21, two mesh members 122 and 124, and a filter paper 123.

The upstream side mesh member 122 is a mesh member through which the coolant 30 and moisture can pass. This upstream side mesh member 122 is made of a conductive material having conductivity. As the conductive material forming the upstream side mesh member 122, a metal material may be cited. Among these, from the viewpoint of suppressing rusting, for example stainless steel or titanium etc. are preferable.

The downstream side mesh member 124, in the same way, is a mesh member formed with numerous pores through which the coolant 30 and moisture can pass. This downstream side mesh member 124 is made of a conductive material having conductivity. As the conductive material forming the downstream side mesh member 124, a metal material may be cited. Among these, from the viewpoint of suppressing rusting, for example stainless steel or titanium etc. are preferable. Note that in the present embodiment, the refilling source container 9 side is called "upstream", while the refilled tank 4 side of the chiller 3 is called "downstream".

These mesh members 122 and 124 are provided inside the tubular member 21 in a stacked state. These mesh members 122 and 124 are provided in the tubular member 21 in a posture that they become substantially perpendicular to the axial direction of the tubular member 21 (direction of flow of coolant 3). All of the coolant 30 passing inside the tubular member 21 from the upstream side toward the downstream side inevitably passes through the mesh members 122 and 124.

The filter paper 123 can hold the moisture contained in the coolant 30 and is sandwiched tightly between the upstream side mesh member 122 and the downstream side mesh member 124. Further, by this filter paper 123 holding moisture, the mesh members 122 and 124 are conductively connected.

Note that the member sandwiched between the mesh members 122 and 124 is not particularly limited to filter paper so long as it has an electric insulation ability and holds moisture. For example, a cloth etc. may also be sandwiched as a holding means between the mesh members 122 and 124.

Furthermore, the tubular member 121 is filled inside it with zeolite 125 at the downstream side of the mesh members 122 and 124 and filter paper 123. Due to this, the moisture contained in the coolant 30 is adsorbed by the zeolite 125 even if passing through the filter paper 123, so it is possible to prevent the moisture from ending up flowing into the tank 4 of the chiller 3. Further, at the time of ordinary use, this zeolite 125 maintains the dryness of the filter paper 123. Note that, instead of zeolite 125, it is also possible to fill a moisture adsorbent which has superior properties of chemical stability and electrical insulation ability. As such a moisture adsorbent, for example silica gel may be cited.

The above explained filter unit 12 is detachably attached through couplers (not shown) to the first and second pipes 11 and 13. Further, after once detecting the entry of moisture into the coolant 30, the filter unit 12 is detached from the couplers and replaced with a new filter unit 12.

The resistance value measurement circuit 16 is a circuit which applies voltage between the upstream side mesh member 122 and the downstream side mesh member 124 to detect any slight current flowing between the mesh members 122 and 124 and thereby measures the resistance value between the upstream side mesh member 122 and downstream side mesh member 124.

When moisture is not mixed in the coolant 30 passing through the filter unit 12, the upstream side mesh member 122 and the downstream side mesh member 124 are electrically insulated by the filter paper 123 and coolant 30, so the resistance value measurement circuit 16 measures an infinitely large resistance value.

As opposed to this, when moisture is mixed in the coolant 30, as shown in FIG. 2, the intermixed moisture is held in the filter paper 123. Further, the upstream side mesh member 122 and the downstream side mesh member 124 are conductively connected through the part 123a of the filter paper 123 trapping the moisture, so the resistance value measurement circuit 16 measures the falling resistance value R.

The relay 17 is a contact which opens and closes a circuit for supplying power to the pump 14 and closes the contact so long as the resistance value measurement circuit 16 measures an infinitely large resistance value. When the resistance value measurement circuit 16 measures the resistance value R, the relay 17 closes the contact. Therefore, when moisture is not mixed in the coolant 30, the pump 14 is supplied with power, while when moisture is mixed in the coolant 30, the supply of power to the pump 14 is stopped.

The alarm device 18 is a device for raising an alarm when moisture is mixed in the coolant 30 passing through the filter unit 12. This alarm device 18 is designed to alert a worker refilling the coolant 30 to the fact that moisture is mixed in the coolant 30 when the resistance value measurement circuit 16 measures the resistance value R.

Below, the operation of the conductive fluid detection apparatus 10 according to the present embodiment will be explained.

First, the front end of the first pipe 11 is inserted into the container 9 in which the coolant 30 is stored and the rear end of the third pipe 15 is inserted into the tank 4 of the chiller 3. Next, the pump 14 is driven and the injection of coolant 30 is started through the first pipe 11, filter unit 12, second pipe 13, pump 14, and third pipe 15 from the container 9 to the tank 4 of the chiller 3.

At the time of this injection, when moisture is mixed in the coolant 30, the filter unit 12 traps the moisture at the filter paper 123, the upstream side mesh member 122 and the downstream side mesh member 124 are conductively connected through the trapped part 123a, and the resistance value between the mesh members 122 and 124 falls from infinitely large to the resistance value R.

If the resistance value measurement circuit 16 measures this resistance value R, the relay 17 opens, and the supply of power to the pump 14 is stopped, and the injection of coolant 30 into the tank 4 of the chiller 3 is forcibly stopped. Due to this, it is possible to prevent the flow of the coolant 30 in which moisture is mixed into the tank 4 of the chiller 3. Further, at the same time as the relay 17 stops the pump 14, an alarm device 18 alerts a worker to the fact that moisture is mixed in the coolant 30.

As opposed to this, when moisture is not mixed in the coolant 30, the resistance value measurement circuit 16 detects an infinitely large resistance value, so the pump 14 is constantly driven and coolant 30 continues being injected from the container 9 to the tank 4 of the chiller 3.

In the above way, in the present embodiment, when moisture mixed in the coolant 30 is held at the filter paper 123 and the mesh members 122 and 124 are conductively connected, it is judged based on this conductive connection that moisture is mixed in the coolant 30 and the pump 14 is stopped, whereby the moisture mixed in the coolant 30 is prevented from flowing into the tank 4 of the chiller 3.

Note that, in the above embodiment, the case where moisture is mixed into the coolant 30 was explained, but the invention can also be applied to the case if mistaking the containers and ending up injecting not the coolant 30, but distilled water or other moisture itself into the tank 4 of the chiller 3. In this case as well, the moisture conductively connects the mesh members 122 and 124. Based on the conductive connection, the pump 14 stops, so it is possible to prevent moisture from entering the tank 4 of the chiller 3.

Second Embodiment

Figure 3:
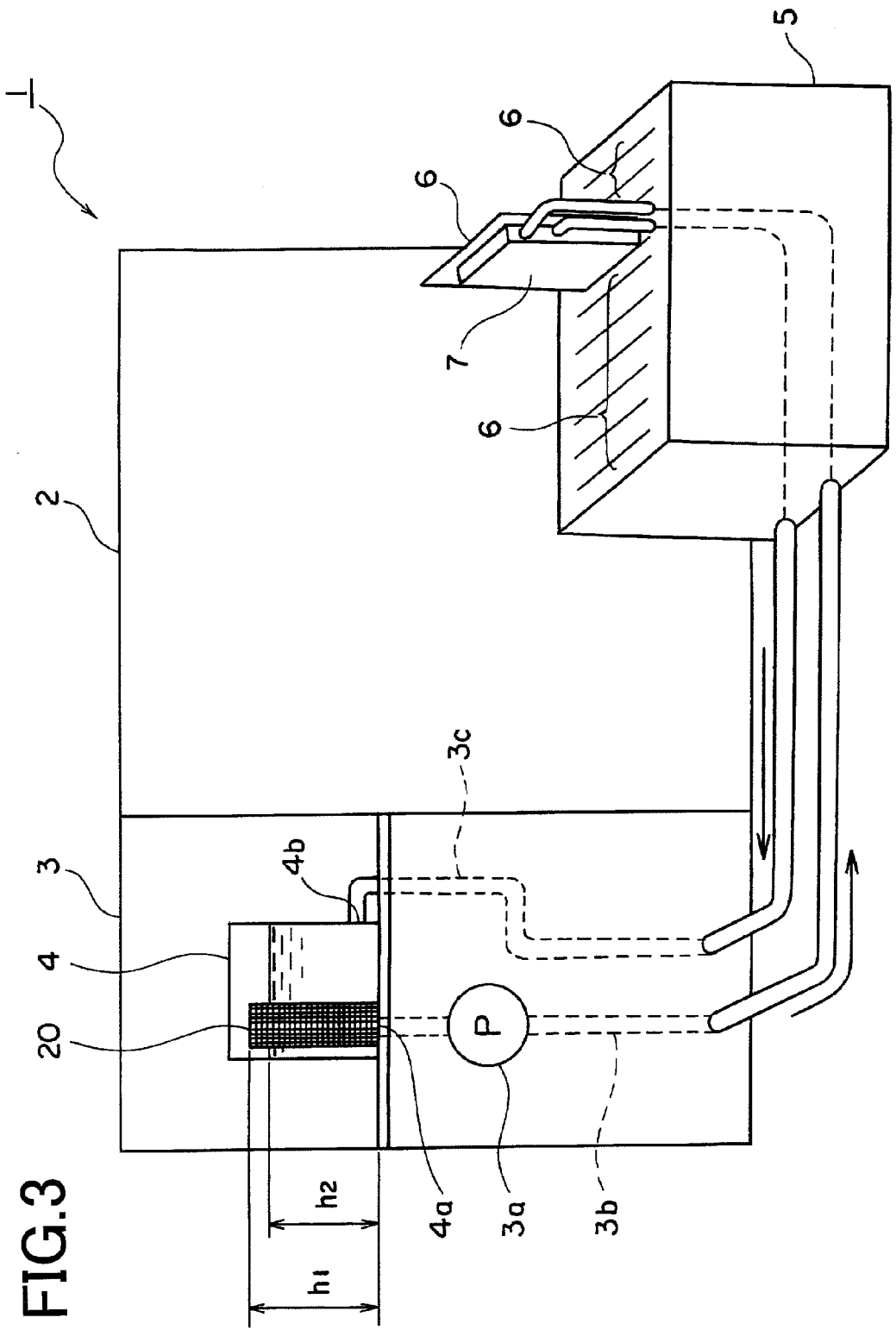
FIG. 3 is a schematic perspective view showing a coolant circulation path of an electronic device test system in a second embodiment of the present invention.
Figure 4:
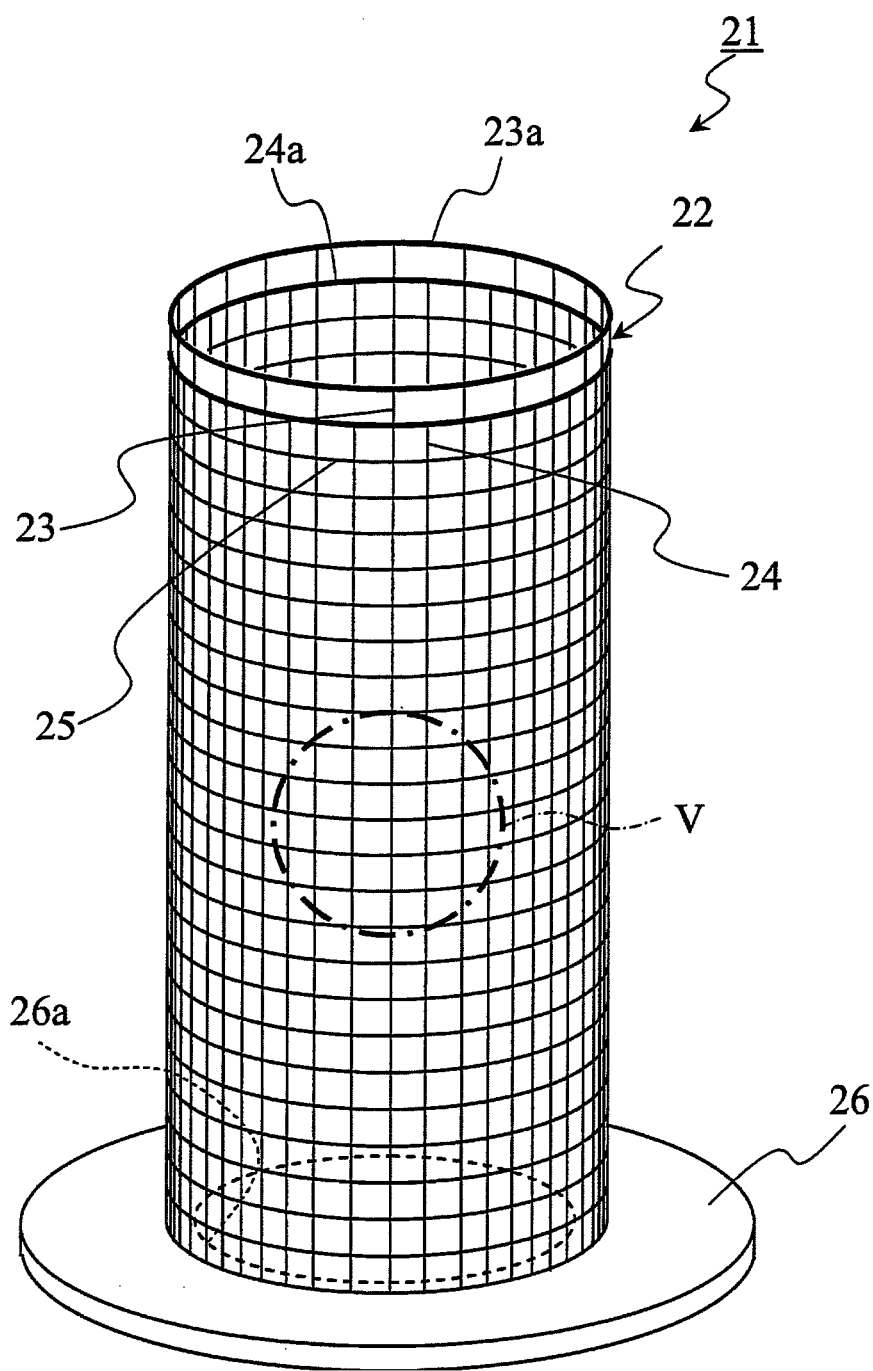
FIG. 4 is a perspective view showing a filter unit according to a second embodiment of the present invention.
Figure 5:
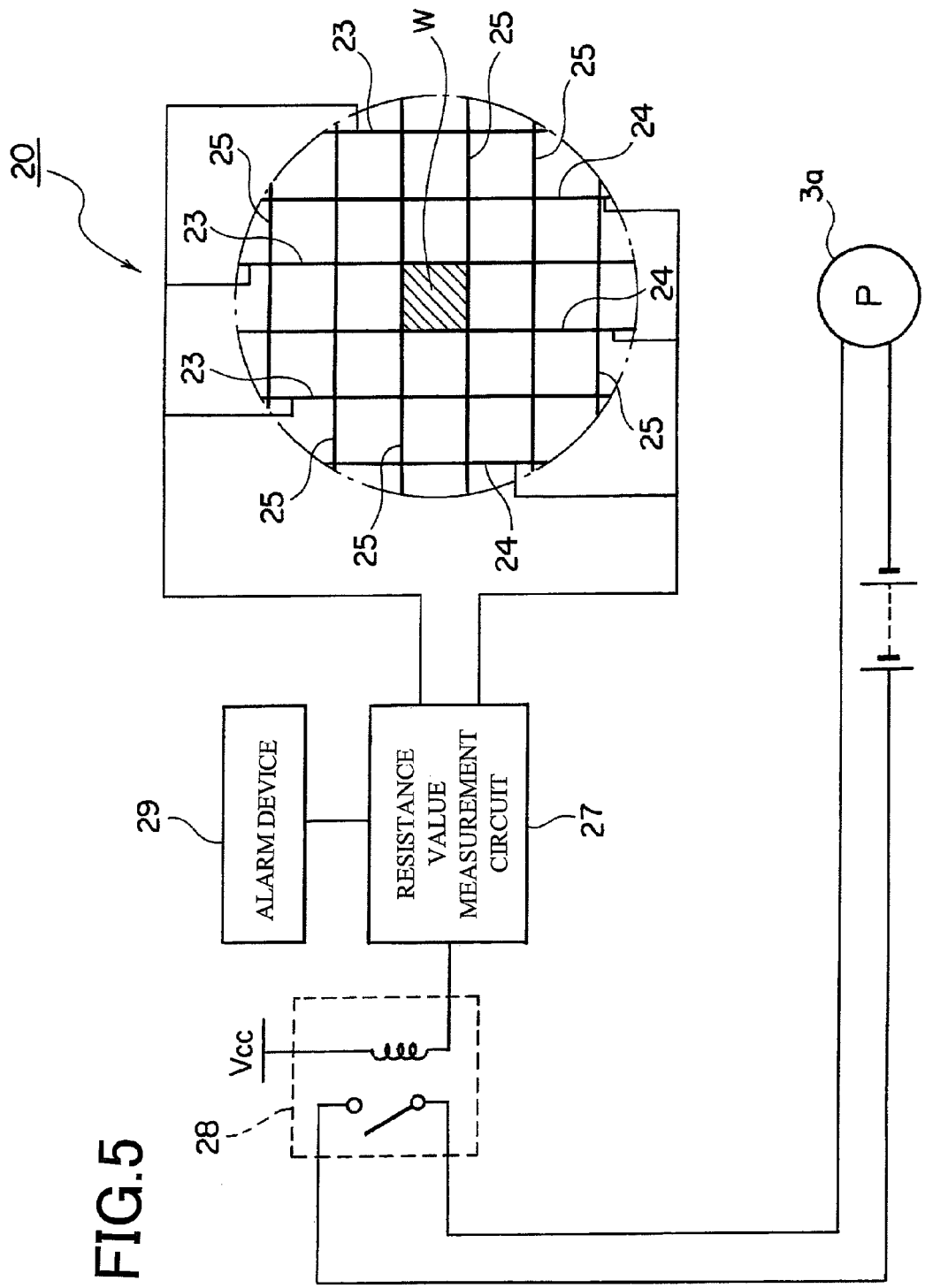
FIG. 5 is an enlarged plan view of a V part of FIG. 4 and a conceptual view showing the overall configuration of a conductive fluid detection apparatus according to a second embodiment of the present invention.
Figure 6:
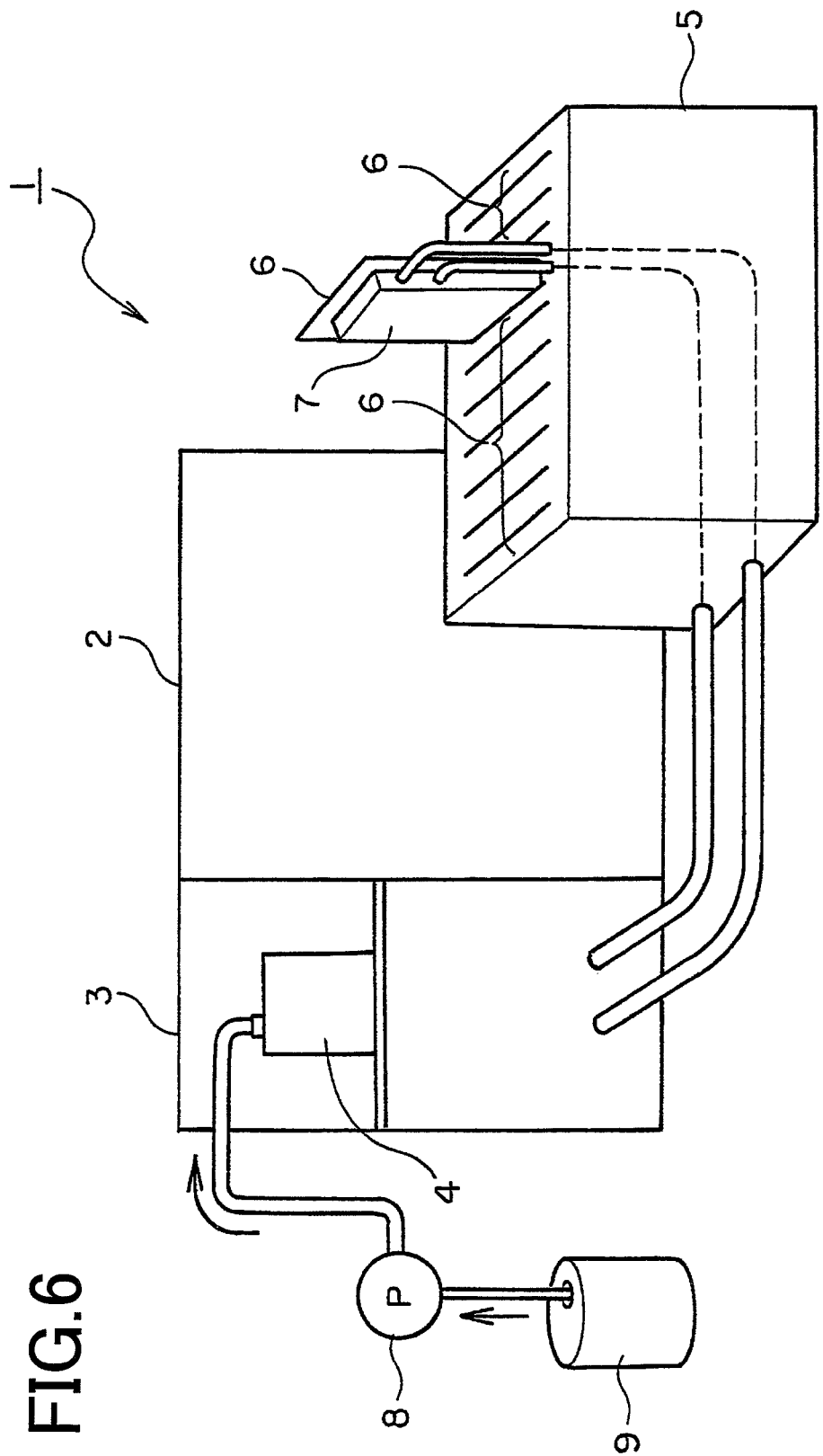
FIG. 6 is a schematic perspective view showing a conventional method of refilling a coolant in a chiller.

FIG. 3 is a schematic perspective view showing a coolant circulation path of an electronic device test system in a second embodiment of the present invention, FIG. 4 is a perspective view showing a filter unit according to the second embodiment of the present invention, and FIG. 5 is an enlarged plan view of a V part of FIG. 4 and a conceptual view showing the overall configuration of a conductive fluid detection apparatus according to the second embodiment of the present invention.

The chiller 3, as shown in FIG. 3, as provided with a pump 3a for circulating the coolant 30 by the path of the tank 4→the supply side pipe 3b→the water jacket 7→the return side pipe 3c→the tank 4. When this pump 3a is driven, the coolant 30 stored in the tank 4 is sucked to the outlet 4a of the tank 4, passes over the above path, then returns to the inside of the tank 4 via the inlet 4b. Note that, while not particularly illustrated, the supply side pipe 3b from the tank 4 to the water jacket 7 passes through the inside of the heat exchanger for cooling the coolant 30 to the desired temperature.

The conductive fluid detection apparatus 20 according to the second embodiment of the present invention is a apparatus for detecting the moisture mixed into the coolant 30 stored in the tank 4 of the chiller 3 when the drive of the pump 3 causes the coolant 30 to be sucked to the outlet 4a of the tank 4. As shown in FIG. 3 to FIG. 5, it comprises a filter unit 21, resistance value measurement circuit 27, relay 28, and alarm device 29. As the coolant 30 stored in the tank 4 of the chiller 3 in the present embodiment, for example, 3M's Fluorinert (registered trademark) or another fluorine-based inert liquid may be cited.

The filter unit 21 in the present embodiment, as shown in FIG. 4, comprises a cylindrical tubular member 21 and a disk shaped mount 26.

The tubular member 22 comprises a mesh member into which a plurality of first conductive wires 23, a plurality of second conductive wires 24, and a plurality of insulating wires 25 are braided together.

The plurality of first conductive wires 23, as shown in the drawing, are arranged at substantially equal intervals along the circumferential direction of the tubular member 22 in a posture extending along the height direction of the tubular member 22. Further, the first conductive wires 23 are electrically connected to a ring-shaped first connecting member 23a at the top end.

The plurality of second conductive wires 24, as shown in the drawing, are arranged at substantially equal intervals along the circumferential direction of the tubular member 22 in a posture extending along the height direction of the tubular member 22. Further, the first conductive wires 23 and the second conductive wires 24 are arranged alternately along the circumferential direction of the tubular member 22. The second conductive wires 24 are electrically connected to a ring-shaped second connecting member 24a at the top end.

Note that, as shown in the drawing, the second conductive wires 24 are shorter than the first conductive wires 23 along the height direction of the tubular member 22. Further, for example, by covering the outer circumference of the second connecting member 24a other than at the connecting points with the second conductive wires 24, the second connecting member 24a is electrically insulated with respect to the first conductive wires 23.

The insulating wires 25 are ring-shaped wires made of for example a synthetic resin material or other material superior in electric insulation. The insulating wires 25 mechanically connect the first conductive wires 23 and the second conductive wires 24 along the circumferential direction in the state maintaining the electric insulation between them.

The mount 26, as shown in FIG. 4, is a disk-shaped member formed with an opening 26a at the center and is, for example, made of a synthetic resin material or other material superior in electric insulation. This mount 26 and tubular member 22 are attached so that the opening 26a of this mount 26 and the inside hole of the tubular member 22 are coaxial.

The above configured filter unit 21, as shown in FIG. 3, is provided inside the tank 4 so that the outlet 4a of the tank 4 and the opening 26a of the mount 26 are coaxial. The tubular member 22 surrounds the outlet 4a. Due to this, all of the coolant 30 heading toward the outlet 4a in the tank 4 passes through the tubular member 22.

As shown in the figures, the height $h_1$ of this filter unit 21 is set higher than the upper limit $h_2$ of the liquid surface of the coolant 30 stored in the tank 4. Due to this, it becomes possible to accurately detect the intermixture of moisture without relying on the change of the liquid surface of the coolant 30 in the tank 4.

The resistance value measurement circuit 27 is a circuit which applies voltage between the first conductive wires 23 and the second conductive wires 24, detects the slight current flowing between the conductive wires 23 and 24, and measures the resistance value between the first conductive wires 23 and the second conductive wires 24. Note that preferably the first conductive wires 23 and the second conductive wires 24 are as close as possible so as to enable detection even with a slight amount of moisture.

When moisture is not mixed in the coolant 30 passing between the first conductive wires 23 and the second conductive wires 24 of the filter unit 21 in the tank 4, the first conductive wires 23 and the second conductive wires 24 are electrically insulated by the coolant 30, so the resistance value measurement circuit 27 measures an infinitely large resistance value.

As opposed to this, when moisture is mixed in the coolant 30, as shown by the enlarged front view of FIG. 5, and the mixed moisture conductively connects the first conductive wires 23 and the second conductive wires 24, the first conductive wires 23 and the second conductive wires 24 are instantaneously conductively connected through the moisture W, so the resistance value measurement circuit 27 detects the resistance value R of the non-insulating state. Here, preferably a latch circuit is provided so as to enable detection of even instantaneous detection signals.

The relay 28 is a contact opening and closing a circuit for supplying power to the pump 3a. So long as the resistance value measurement circuit 27 measures a high resistance value (insulation resistance value) showing an insulated state, the relay 28 closes the contact. If the resistance value measurement circuit 27 measures the desired resistance value R (non-insulation resistance value) or less, the relay 28 closes the contact. Therefore, when moisture is not mixed in the coolant 30, the pump 3a is supplied with power, while when moisture is mixed in the coolant 30, the supply of power to the pump 3a is immediately cut off. Note that, in the present embodiment, as shown in FIG. 5, the explanation was given of the example of application to a DC power supply, but the present invention is not particularly limited to this and may also be applied to an AC power supply. Further, the pump startup control unit for controlling the startup/shutdown of the pump 3a is not particularly illustrated.

The alarm device 29 is a device which, when detecting that moisture has entered the coolant 30 passing through the filter unit 21, immediately notifies that, for example, by a display device or warning device or via a network. This alarm device 29 is designed to alert for example the operator of an electronic device test system 1 to the fact that moisture is mixed in the coolant 30 when the resistance value measurement circuit 27 measures the resistance value R.

Below, the operation of the conductive fluid detection apparatus 20 according to the present embodiment will be explained.

When the power supply (not shown) of the chiller 3 is turned on and the pump 3a is driven, the coolant 30 stored in the tank 4 is sucked toward the outlet 4a and supplied to the circulation system comprising the supply side pipe 3b→the water jacket 7→the return side pipe 3c→the tank 4.

When the drive operation of the pump 3a causes the coolant 30 to head toward the outlet 4a, all of the coolant 30 passes through the mesh of the tubular member 22 of the filter unit 21.

At the time of this passage, if the coolant 30 contains a slight amount of moisture, that moisture will cause the first conductive wires 23 and the second conductive wires 24 to enter a non-insulating state and as a result the resistance value between these conductive wires 23 and 24 will fall from infinitely large to a resistance value R.

When the resistance value measurement circuit 27 measures this resistance value R, the relay 28 opens, the supply of power to the pump 3a is stopped, and the circulation of the coolant 30 in the chiller 3 is stopped. Due to this, the coolant 30 in which the moisture is mixed can be prevented from flowing out from the tank to the circulation system of the chiller 3. At the same time as stopping the pump 3a by the relay 28, the alarm device 29 warns the operator that moisture is mixed in the coolant 30 stored in the tank 4.

On the other hand, when moisture is not mixed in the coolant 30, the electric insulation between the first conductive wires 23 and the second conductive wires 24 forming the mesh is maintained by the coolant 30, and the resistance value measurement circuit 27 detects a substantially infinitely large resistance value, so the pump 3a is constantly driven and the coolant 30 continues to be circulated in the chiller 3.

Note that the above explained embodiments were described for facilitating the understanding of the present invention and were not described for limiting the present invention. Therefore, the elements disclosed in the above embodiments include all design modifications and equivalents falling under the technical scope of the present invention.

The filter unit 21 in the present embodiment was structured with its top part open, but the present invention is not limited to this. For example, the top part of the filter unit may also be plugged by an insulating member. In this case, there is the advantage that the operation is not dependent on the upper limit $h_2$ of the liquid surface of the coolant 30.

Further, if the insulating fluid in the present invention is a fluid having a high insulating property and chemically stable properties, it is not limited to a fluorine-based inert liquid as explained by the embodiments.

Further, in the above embodiments, the pump 14 was explained as an electrically driven one, but the present invention is not particularly limited to this. It may also be a pump manually operated by a worker. In this case, the worker stops the operation of the pump based on an alarm of the alarm device 18.

Furthermore, the resistance value measurement circuit 27 may have a function of identifying as a defect of the filter unit 21 and issuing an alarm on this defective state to the outside when detecting a resistance value (for example several hundred Ω) much lower than the resistance value due to the moisture detection. Due to this, it possible to prevent bungle due to short-circuits between adjoining first and second conductive wires 23 and 24.

The invention claimed is:

1. An electronic device test apparatus comprising:
a filter unit;
a tank in which an insulating fluid is stored;
a water jacket which covers a testing device mounted on a board;
a supply side pipe which connects the tank and the water jacket;
a return side pipe which connects the water jacket and the tank;
a pump configured to circulate the insulating fluid through the tank, the supply side pipe, the water jacket, and the return side pipe; and
a judging device configured to judge that a conductive fluid is mixed into the insulating fluid when the conductive members are conductively connected, wherein
the filter unit comprises two or more conductive members made of a conductive material and enabling passage of the insulating fluid and the conductive fluid,
the two or more conductive members are provided inside the tank so that the insulating fluid heading toward an outlet of the tank can pass through the two or more conductive members,
the two or more conductive members include first conductive members and second conductive members extending along the height direction,
the first conductive members and the second conductive members are arranged alternately along the circumferential direction, and
the judging device stops the pump when detecting the inclusion of the conductive fluid into the insulating fluid.

2. The electronic device test apparatus as set forth in claim 1, wherein the two or more conductive members are provided so as to surround the outlet.

3. The electronic device test apparatus as set forth in claim 2, wherein the two or more conductive members form a tubular member so as to surround the outlet, and
a topmost end of the tubular member is set higher than an upper limit of the liquid surface of the insulating fluid stored in the tank.

4. The electronic device test apparatus as set forth in claim 1, wherein
the tubular member has insulating members extending along the circumferential direction, and
the insulating members connect the first conductive members and the second conductive members along the circumferential direction.

5. The electronic device test apparatus as set forth in claim 1, wherein the insulating fluid includes a fluorine-based inert liquid, and the conductive fluid includes water.

6. The electronic device test apparatus as set forth in claim 1, wherein the judging device judges the inclusion of the conductive fluid into the insulating fluid based on a resistance value between the conductive members.

7. The electronic device test apparatus as set forth in claim 1, further comprising an alarm device configured to issue an alarm when the judging device detects the inclusion of the conductive fluid into the insulating fluid.

* * * * *